United States Patent [19]

Turner, Sr.

[11] Patent Number: Plant 6,339

[45] Date of Patent: Oct. 18, 1988

[54] *NERIUM OLEANDER* PLANT — TURNER'S CARNIVAL

[76] Inventor: Ted L. Turner, Sr., 6503 S. Padre Island Dr., Corpus Christi, Tex. 78412

[21] Appl. No.: 906,410

[22] Filed: Sep. 12, 1986

[51] Int. Cl.[4] ..... A01H 5/00

[52] U.S. Cl. ..... Plt./54

[58] Field of Search ..... Plt./54

*Primary Examiner*—Robert E. Bagwill

*Attorney, Agent, or Firm*—Stewart N. Rice

[57] ABSTRACT

A *Nerium oleander* plant which has a petite and upright habit of fairly rapid growth, being particularly characterized by the unique color of its inflorescence, the flowers being a soft pink color with tinges of pinkish red.

1 Drawing Sheet

DESCRIPTION OF THE INVENTION

The present invention relates to a new and distinct variety, of petite size, of *Nerium oleander* which was originated by me as a seedling by successive selection and crossing. I originally started from a *Nerium oleander* "Mrs. Roeding" and a *Nerium oleander* "Petite salmon". The "Mrs. Roeding" produces a salmon pink semi-double flower, the plant being dwarf in size, that is about six to eight feet tall at maturity. The "Petite salmon" produces single flowers which are bright salmon pink in color, and is a petite size plant about six feet high at maturity. From a seedling which was a cross from the "Mrs. Roeding" and the "Petite salmon", I further crossed with a *Nerium oleander* "Algiers". The "Algiers" is a petite size plant which produces a single flower of fluorescent red color. However in making my crosses, I observed that pollination was sometimes accomplished by bees from unknown plants. Thus unknown parentage could have been introduced by the bees even though I did not purposely introduce any parentage other than the "Mrs. Roeding", the "Petite Salmon" and the "Algiers".

The new and distinct variety of *Nerium oleander* claimed by me herein was developed through several generations of selection and crossing. From one group of seedlings I observed a plant, being the plant claimed herein, having a new and distinct color of flowers, and from cuttings of such plant I was able to asexually reproduce plants having the same characteristics and flower color as the original seedling. All of the descendant plants showed the same characteristics as the original seedling, and as a result of extensive observations and tests which are not described in full herein for sake of brevity, it is my opinion and I am convinced that my new plant is a new variety of *Nerium oleander* which is distinguished from all other varieties of which I am aware as evidenced by the following unique combination of principal characteristics which are outstanding therein:

(1) An upright habit of fairly rapid growth and of petite size making it especially suitable for use as a low hedge, as a pot plant or to add garden color;

(2) An ability to be asexually reproduced;

(3) The ability to flower off and on throughout the year;

(4) The ability to bloom in partial shade, such as morning sun only; and (5) The ability to grow and flower in relatively small pots as small as about eight centimeters in diameter.

(6) The ability to produce a flower having a soft pink color and tinges of pinkish red.

Asexual reproductions of my new variety as by cuttings shown that the foregoing characteristics and distinctions come true to form and are established and transmitted through succeeding propagations.

The accompanying FIGURE is a photograph of a typical flower on the plant of my new variety more clearly illustrating the colors present on each flower. The true color of the foliage and flowers is described in the following description and is depicted in the FIGURE which depicts the color as nearly as true as is reasonably possible in a color illustration of this type.

The following is a detailed description of my new variety of *Nerium oleander,* which color numbers in accordance with the Pantone Matching System of colors for printing inks, 18th edition, published by Pantone, Inc., 1985–1986. Terms used to describe colors are those of ordinary significance.

THE PLANT

Growth habit: Upright, petite size; the height of an unpruned mature plant will probably be from about 2 to 3 meters, but has not yet been determined; fast growing. The plant grows full from just about ground level upward, with the width of the plant about 30% to 60% of the height.

Hardiness: Adapted to seaside planting as it tolerates soil with relatively high salt content; tolerates droughts; will not withstand prolonged and severe freezing weather; most suitable for the Southern United States from California to Florida, in the areas known as Zones 9 and 10; withstands heat and light and grows either in full sun or in partial shade (up to 50% shade) such as morning sun only; can be grown in small pots as small as about 8 centimeters in diameter.

Branches: The plant is loosely branched from just above ground level with main branches and branchlets ascending. The plant does not develop a central leader or trunk. New growth of branches is a light to medium green, Color No. 390U, changing to light brown in color as branches mature.

Blooming period: Blooms off and on the entire year, being in bloom about 75% of the time.

THE FOLIAGE

Type: Broadleaf evergreen; numerous; petioled; grow in a whorl with three leaves in each whorl.

Shape: Linear-lanceolate, with entire margins. Apex is more or less acuminate and slightly non-symmetrical, and base is acute.

Petioles: Length, from about 4 to 6 mm; color pale green.

Leaf size: Length of mature leaf from about 120 to 160 mm; width of mature leaf about 15 to 25 mm. Size of leaf varies according to sunshine conditions at the time the leaf is produced, with larger leaves being produced under cloudy conditions than under sunny conditions.

Venation: Midrib or under surface prominent and readily apparent and is pale green, Color No. 585U; on upper surface midrib is clearly visible and slightly recessed, and is pale green, Color No. 585U; lateral veins are not readily apparent on upper surface but under surface contains numerous, delicate, almost parallel lateral veins which are readily apparent, the lateral veins being substantially perpendicular to the midrib.

Leaf color:

*Mature leaves.*—Upper surface— dark green, Color No. 574C; under surface much lighter in color than upper surface, being a medium green, Color No. 582U.

New leaves: About the same color as mature leaves but perhaps slightly lighter in color.

Leaf texture: Tough, leathery; smooth.

*Upper surface.*—semi-glossy.

*Lower surface.*—Dull.

THE INFLORESCENCE

Position and abundance: Flowers cluster at twig or branch ends in terminal cymes, with cymes appearing at various positions from the lower part to the upper part of the plant.

Form: Single; regular; pediceled; petals united in a sympetalous corolla; salverform; tube spreads into five limbs or lobes; each flower is about 35 to 45 mm across; corona conspicuous at junction of tube and spreading limb, corona about 10 to 15 mm in diameter and much shorter than spreading limbs, the corona having five crownlike appendages, each appendage corresponding to a limb, each appendage being 2 to 4 toothed;

Buds: Limbs convolute in the bud, obliquely apiculate, the folds twisting counterclockwise when viewing down onto the tip of the bud.

Calyx: Of 5 persistent sepals, imbricate in the bud, lanceolate, acuminate, about 4 to 6 mm long.

Stamen: 5 stamens; filaments partly adnate to corolla tube; anthers with 2 basal tails, apex long-attenuate, hairy.

Color of flower: Limbs of the corolla in new flowers are soft pink color, Color No. 197C, except that one edge of the margin of each limb (as viewed from the topside of the flower) is tinged with pinkish red, Color No. 207C, the edge of each limb that is tinged with pinkish red being that edge which is exposed in the bud. As the flowers age, the color of the limbs fade somewhat becoming more pale than in the new growth. The corona is golden yellow, Color No. 114U, with 5 groups of 3 dark pinkish red streaks, Color No. 199U, each group of pinkish red streaks consisting of a thicker central streak having a narrower streak on each side, each group of pinkish red streaks being more or less centered with and corresponding to limb and to a said corona appendage, the streaks being radial in nature (as opposed to circular) such that the streaks extend from the edge of each appendage down into the corona tube, or vice versa. The outside of the corolla tube of each flower is pale pink, Color No. 197U, with tinges of pale yellow, Color No. 113U, there being in particular 5 small pale yellow streaks extending along the tube alternate with the spreading limbs. The calyx and sepals are light green, Color No. 382U, with tinges of pinkish red, Color No. 207C.

Color of buds: Dark pinkish red, Color No. 207C, corresponding to edges of the convoluted limbs.

To further describe my new variety of *Nerium oleander,* it is very similar in size and growth habit to the other well-known petite size *Nerium oleanders* which grow in an upright manner, except for the color of the flowers, and except that my new variety appears to tolerate shade better than the other petite *Nerium oleanders* of which I am aware. My new variety also blooms much earlier, and longer, than other petite *Nerium oleanders* of which I am aware and blooms more profusely with each cluster or terminal cyme appearing to have more blooms per cluster than prior art petites of which I am aware. I am not aware of any *Nerium oleander* of petite size having a flower which is the same as that produced by my plant.

VARIETY NAME

The proposed variety name of my new plant is *Nerium oleander* "Turner's Carnival".

I claim:

1. A new and distinct variety of petite size *Nerium oleander* substantially as shown and described, having an upright habit of fairly rapid growth making it especially suitable as a low hedge or pot plant, having an ability to be asexually reproduced, having the ability to flower off and on throughout the entire year, having the ability to grow in full sun or in partial shade, having the ability to grow and flower in relatively small pots, and being particularly characterized by its petite size combined with the unique color of its inflorescence, the flowers being a soft pink color with tinges of pinkish red.

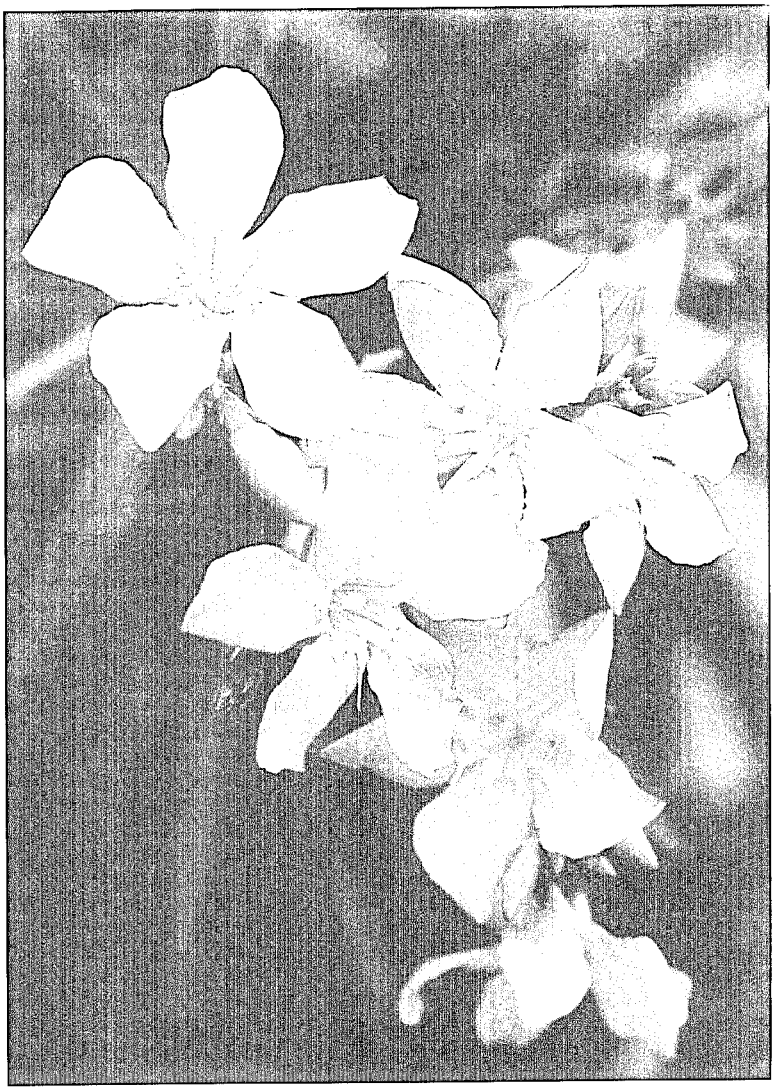

* * * * *